United States Patent
Goldsmith et al.

(10) Patent No.: US 9,223,156 B2
(45) Date of Patent: Dec. 29, 2015

(54) FREE-SPACE LASER TUNING OF OPTICAL MICROCAVITIES

(71) Applicant: Wisconsin Alumni Research Foundation, Madison, WI (US)

(72) Inventors: Randall Howard Goldsmith, Madison, WI (US); Kevin Daniel Heylman, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 10 days.

(21) Appl. No.: 14/180,778

(22) Filed: Feb. 14, 2014

(65) Prior Publication Data

US 2015/0234211 A1    Aug. 20, 2015

(51) Int. Cl.
*G02F 1/01* (2006.01)
*G02B 6/26* (2006.01)
(Continued)

(52) U.S. Cl.
CPC .......... *G02F 1/0147* (2013.01); *G01N 21/7746* (2013.01); *G02B 6/26* (2013.01); *G02B 6/29341* (2013.01); *G02F 1/01* (2013.01); *G02F 1/0118* (2013.01); *H01S 3/05* (2013.01); *H01S 3/06* (2013.01); *H01S 3/08* (2013.01); *H01S 3/30* (2013.01); *B41M 5/382* (2013.01); *B82Y 20/00* (2013.01); *G02B 6/243* (2013.01); *G02F 1/0115* (2013.01); *H01S 3/0627* (2013.01)

(58) Field of Classification Search
CPC ......... G02F 1/01; G02F 1/011; G02F 1/0115; G02F 1/0118; G01N 21/7746; B82Y 20/00; B41M 5/382; G02B 6/243; G02B 6/26; G02B 6/29341; G02B 6/29343; G02B 6/29391; G02B 6/42; H01S 3/05; H01S 3/06; H01S 3/0627; H01S 3/063; H01S 3/067; H01S 3/08; H01S 3/30
USPC ................ 359/288; 350/339.07, 343; 73/643; 156/235; 257/98, 432, E33.069; 436/57, 164, 165; 422/82.05; 427/146
See application file for complete search history.

(56) References Cited

U.S. PATENT DOCUMENTS 6,521,324 B1 * 2/2003 Debe et al. .................... 156/235
6,633,696 B1 * 10/2003 Vahala et al. .................. 385/27
(Continued)

OTHER PUBLICATIONS

Arbouet et al., Direct Measurement of the Single-Metal-Cluster Optical Absorption, Physical Review Letters, vol. 93, No. 12, Sep. 14, 2004, pp. 127401-1-127401-4.

(Continued)

*Primary Examiner* — Loha Ben
(74) *Attorney, Agent, or Firm* — Bell & Manning, LLC (57) ABSTRACT

Methods and apparatuses for resonance tuning of microcavities are provided. An apparatus comprises a whispering gallery mode optical microcavity characterized by at least one resonance frequency; optical components configured to evanescently couple a probe laser beam into the microcavity; an absorber element in thermal contact with the microcavity; and optical components configured to illuminate the absorber element with a free space pump light beam, wherein the absorber element is configured to absorb energy from the free space pump light beam, thereby generating heat, and to transfer the heat to the microcavity, thereby inducing a shift in the at least one resonance frequency. The absorber element may be configured as a pillar forming an interfacial region with the microcavity at one of the ends of the pillar. The surface of the microcavity may be substantially free of a coating material.

20 Claims, 9 Drawing Sheets

(51) Int. Cl.
*H01S 3/08* (2006.01)
*G02B 6/293* (2006.01)
*G01N 21/77* (2006.01)
*H01S 3/05* (2006.01)
*H01S 3/06* (2006.01)
*H01S 3/30* (2006.01)
*G02B 6/24* (2006.01)
*B82Y 20/00* (2011.01)
*B41M 5/382* (2006.01)

(56) References Cited

U.S. PATENT DOCUMENTS

| | | | | |
|---|---|---|---|---|
| 6,741,628 | B2* | 5/2004 | Painter et al. | 372/92 |
| 6,777,244 | B2* | 8/2004 | Pepper et al. | 436/165 |
| 7,384,797 | B1* | 6/2008 | Blair | 436/524 |
| 7,781,217 | B2 | 8/2010 | Armani et al. | |
| 8,597,577 | B2* | 12/2013 | Flagan et al. | 422/82.11 |
| 8,957,445 | B2* | 2/2015 | Senellart et al. | 257/98 |
| 2014/0290370 | A1* | 10/2014 | Hossein-Zadeh, Mani | 73/643 |

OTHER PUBLICATIONS

Rokhsari et al., Ultralow Loss, High Q, Four Port Resonant Couplers for Quantum Optics and Photonics, Physical Review Letters, vol. 92, No. 25, Jun. 25, 2004, pp. 235905-1-253905-4.

Tapalian et al., Thermooptical Switches Using Coated Microsphere Resonators, IEEE Photonics Technology Letters, vol. 14, No. 8, Aug. 2002, pp. 1118-1120.

Pan et al., Aligning microcavity resonances in silicon photonic-crystal slabs using laser-pumped thermal tuning, Applied Physics Letters, vol. 92, No. 103114, Mar. 12, 2008, pp. 1-3.

Topolancik et al., Photoinduced Transformations in Bacteriorhodopsin Membrane Monitored with Optical Microcavities, Biophysical Journal, vol. 92, Mar. 2007, pp. 2223-2229.

Armani et al., Label-Free, Single-Molecule Detection with Optical Microcavities, Science, vol. 317, Aug. 10, 2007, pp. 783-787.

Benson et al., Micro-Optical Resonators for Microlasers and Integrated Optoelectronics: Recent advances and future challenges, Frontiers of Planar Lightwave Circuit Technology: Design, Simulation and Fabrication, 2005, pp. 39-70.

Yoshie et al., Optical Microcavity: Sensing down to Single Molecules and Atoms, Sensors, vol. 11, Feb. 7, 2011, pp. 1972-1991.

Righini et al., Whispering gallery mode microresonators: Fundamentals and applications, Rivista Del Nuovo Cimento, vol. 34, No. 7, 2011, pp. 435-488.

Heylman et al., Photothermal mapping and free-space laser tuning of toroidal optical microcavities, Applied Physics Letters, vol. 103, No. 211116, Nov. 21, 2013, pp. 1-4.

Heylman et al., Single-Molecule Absorption Spectroscopy Using Toroidal Optical Microcavities, presentation, UW Madison, May 2013.

* cited by examiner

FREE-SPACE LASER TUNING OF OPTICAL MICROCAVITIES

REFERENCE TO GOVERNMENT RIGHTS

This invention was made with government support under N66001-12-1-4215 awarded by the US Navy. The government has certain rights in the invention.

BACKGROUND

Whispering-Gallery Mode (WGM) optical microcavities are rich experimental platforms for quantum optics, photonics, and sensing. Ultrahigh-Quality factor (Q) toroidal optical microcavities are particularly suited for nonlinear optics and single particle detection, due to their combination of extremely narrow linewidths and small mode volumes. Sensing applications typically entail detection of analyte binding via small shifts in the resonance wavelength, resonator Q-factor, or mode splitting. One advantage of the toroidal geometry is the simplified mode structure relative to other microresonator geometries, which leads to widely separated resonances. However, the high finesse ($10^6$) presents a significant experimental difficulty. The absolute resonant wavelengths are determined by minor variations in the fabrication conditions. In particular, laser-induced reflow, a crucial fabrication step, relies upon a runaway thermal process, although larger diameter toroids have been produced without this step. Typically, tunable external-cavity diode lasers are used to couple light into the resonator, as they possess narrow linewidth and wavelength tunability greater than the resonator's free spectral range (FSR). However, the need for expensive tunable light sources impedes applications that require low-cost fabrication or integration into massively parallel device architecture.

Progress has been made in controlling absolute resonance position in WGM microcavities. These efforts include chemical etching and UV irradiation, though these processes are irreversible, and have not been demonstrated with microtoroids. The entire silicon chip can be heated, although this approach cannot achieve independent control of multiple toroids and is limited by slow switching speeds. A photochromic thin film can be optically pumped to photothermally heat the resonator, but is slowed by the recovery time of the molecule's ground state (~11 s). (See J. Topolancik and F. Vollmer, Appl. Phys. Lett. 89, 184103 (2006).) Similarly, a highly absorbing polymer film can be applied to a microsphere and optically pumped, but with limited tuning range (25 pm) and speed (165 ms). (See H. C. Tapalian, J. P. Laine, and P. A. Lane, IEEE Phot. Tech. Lett. 14, 1118 (2002).) Toroids can be individually functionalized with a heating element, but this approach increases fabrication complexity. (See D. Armani, B. Min, A. Martin, and K. J. Vahala, Appl. Phys. Lett. 85, 5439 (2004).) A second fiber-coupled light source can be used to photothermally tune the resonance, but requires high powers due to the transparency of fused silica at the pump wavelength and is consequently limited to a narrow tuning range. The need for two tunable narrow-linewidth sources also adds cost and complexity. (See J. G. Zhu, S. K. Ozdemir, L. N. He, and L. Yang, Appl. Phys. Lett. 99, 171101 (2011).)

SUMMARY

Provided are methods for tuning the resonance frequencies of optical microcavities, applications for the tuning methods and apparatuses for carrying out the methods and applications.

In one aspect, an apparatus comprises a whispering gallery mode optical microcavity, the microcavity characterized by at least one resonance frequency; optical components configured to evanescently couple a probe laser beam into the microcavity; an absorber element in thermal contact with the microcavity; and optical components configured to illuminate the absorber element with a free space pump light beam, wherein the absorber element is configured to absorb energy from the free space pump light beam, thereby generating heat, and to transfer the heat to the microcavity, thereby inducing a shift in the at least one resonance frequency. In one embodiment, the absorber element is configured as a pillar forming an interfacial region with the microcavity at one of the ends of the pillar. In another embodiment, the surface of the microcavity is substantially free of a coating material.

In another aspect, a method comprises evanescently coupling a probe laser beam into a whispering gallery mode optical microcavity, the microcavity characterized by at least one resonance frequency; and illuminating an absorber element in thermal contact with the microcavity with a free space pump light beam, the absorber element configured to absorb energy from the free space pump light beam, thereby generating heat, and to transfer the heat to the microcavity, thereby inducing a shift in the at least one resonance frequency. In one embodiment, the absorber element is configured as a pillar forming an interfacial region with the microcavity at one of the ends of the pillar. In another embodiment, the surface of the microcavity is substantially free of a coating material.

Other principal features and advantages of the invention will become apparent to those skilled in the art upon review of the following drawings, the detailed description, and the appended claims.

BRIEF DESCRIPTION OF THE DRAWINGS

Illustrative embodiments of the invention will hereafter be described with reference to the accompanying drawings, wherein like numerals denote like elements.

FIGS. 3A-3B show the photothermal map of the spatial dependence of resonance shift for the structure of FIG. 1. The map is constructed from 13×13 grid with 4 μm increment, where each shift at constant (4.2 mW absorbed) pump power is referenced to the shift with no external pump. In FIG. 3B, white dotted lines representing the outline of the toroid and black dotted lines representing the outline of the pillar are superimposed on the map, showing the correlation between maximum shift and the silicon pillar.

FIGS. 4A-4B show the photothermal map of the spatial dependence of resonance shift for the structure of FIG. 2. The map is constructed from 13×13 grid with 4 μm increment, where each shift at constant (4.2 mW absorbed) pump power is referenced to the shift with no external pump. In FIG. 4B, white dotted lines representing the outline of the toroid and black dotted lines representing the outline of the pillar are superimposed on the map, showing the correlation between maximum shift and the silicon pillar.

DETAILED DESCRIPTION

Provided are methods for tuning the resonance frequencies of optical microcavities, applications for the tuning methods and apparatuses for carrying out the methods and applications.

In one aspect, a method is provided which comprises evanescently coupling a probe laser beam into a whispering gallery mode optical microcavity, the microcavity characterized by at least one resonance frequency and illuminating an absorber element in thermal contact with the microcavity with a free space pump laser beam, whereby heat generated via energy absorbed by the absorber element from the free space pump laser beam is transferred to the microcavity to induce a shift in at least one resonance frequency. The phrase "at least one resonance frequency" encompasses an embodiment in which all the resonance frequencies of the microcavity are shifted.

A variety of optical microcavities may be used, provided the microcavity is capable of supporting whispering gallery modes, electromagnetic waves which propagate at the edge of the microcavity. A microcavity may be characterized by its resonance frequencies, those frequencies at which light can be most strongly coupled into the microcavity. A microcavity may be characterized by its quality factor, Q, which equals $\lambda/\Delta\lambda$, where $\lambda$ is the wavelength at which a resonance occurs and $\Delta\lambda$ is the linewidth of the resonance at the resonant wavelength. The microcavities may assume a variety of shapes and dimensions and may be formed from a variety of transparent materials, depending upon the desired characteristic, e.g., resonance frequencies, quality factor, etc. By transparent it is meant that the material is substantially transparent at the resonance frequency or frequencies of the microcavity. Suitable exemplary shapes include a sphere, a cylinder, a toroid, a disk or a bottle. Suitable exemplary transparent materials include a variety of semiconductors, glasses and crystals, e.g., GaAs, silicon, silica, $CaF_2$, $MgF_2$ or $LiNbO_3$. In some embodiments, the microcavity is characterized by a Q of at least about $10^7$. This includes embodiments in which the microcavity is characterized by a Q of at least about $10^8$, at least about $10^9$, or at least about $10^{10}$. In some embodiments, the microcavity is uncoated, by which it is meant that the surface of the microcavity is substantially free of a coating material, e.g., a layer of a polymer, a layer of a biological material, a layer of silica, etc.

The absorber element is in thermal contact with the optical microcavity. The absorber element may be configured to absorb energy from the free space pump laser beam, thereby generating heat, and to transfer the heat to the microcavity, thereby inducing a shift in at least one resonance frequency of the microcavity. Suitable configurations include a variety of geometries and dimensions selected to achieve a particular shift in the resonance frequency of the microcavity and/or a particular resonance tuning property (e.g., tuning ratio or switching speed, which are further described below). In particular, the shape and dimensions may be selected to achieve a desired temperature increase of the microcavity, a desired rate of transfer of heat to the microcavity, and/or a desired thermal equilibration time of the microcavity. A suitable exemplary shape of the absorber element is a pillar forming an interfacial region with the microcavity at one of the ends of the pillar. The other end of the pillar may form an interfacial region with an underlying substrate. The pillar may be characterized by a width, which may be taken as the smallest dimension across the interfacial region between the pillar and the microcavity. If the shape of this interfacial region (which is not particularly limited) is circular, the width may be referred to as a diameter. The pillar may also be characterized by the area of the interfacial region between the microcavity and one of the ends of the pillar. The pillar may further be characterized by a height, taken as the dimension along an axis perpendicular to the interface with the microcavity. The dimensions of the pillar at the interface with the microcavity may be different from the dimensions of the pillar at its opposing end. (See FIGS. 1 and 2, further described below.) However, pillars having uniform dimensions along their heights may also be used. The Example, below, describes how the shape and dimensions of a pillar, including the diameter of a pillar, can be adjusted to achieve a particular temperature increase of the microcavity, rate of heat transfer to the microcavity and thermal equilibration time of the microcavity and therefore, a particular resonance shift, tuning ratio and switching speed.

In some embodiments, the width of the pillar is no more than about 20 µm. This includes embodiments in which the width of the pillar is no more than about 15 µm, no more than about 10 µm, no more than about 5 µm, or no more than about 2 µm. In some embodiments, the width of the pillar is in the range of from about 1 µm to about 50 µm. This includes embodiments in which the width of the pillar is in the range of from about 10 µm to about 40 µm or from about 20 µm to about 40 µm, or from about 25 µm to about 35 µm. In some embodiments, the area of the interfacial region between the pillar and the microcavity is no more than about 300 µm². This includes embodiments in which the area is no more than about 175 µm², no more than about 80 µm², no more than about 20 µm², or no more than about 3 µm². In some embodiments, the area of the interfacial region between the pillar and the microcavity is in the range of from about 1 µm² to about 2000 µm². This includes embodiments in which the area is in the range of from about 80 µm² to about 1250 µm² or from about 300 µm² to about 1250 µm², or from about 500 µm² to about 1000 µm².

The absorber element may be configured from a variety of materials. Typically, the absorber element is composed of a material which is different from the material of the microcavity. The absorber element is desirably composed of a material having a sufficiently high absorption coefficient at the selected wavelength of the free space pump laser beam in order to maximize absorption from the free space pump laser beam. The absorber element may be composed of a material having a sufficiently low absorption coefficient at the selected wavelength of the probe laser beam to minimize absorption from the probe laser beam. For example, the absorber element may be composed of a material which is substantially transparent at the selected wavelength of the probe laser beam. However, since the geometry of the absorber element may be adjusted to minimize or prevent physical contact with the propagating mode in the microcavity, thereby minimizing absorption from this mode, materials which would otherwise absorb some energy from the probe laser beam may be used. The absorber element may be composed of a material having a sufficiently high thermal conductivity in order to maximize heat transfer to the microcavity. Suitable exemplary materials for the absorber include silicon, GaAs, germanium and colored polymers. Colored polymers include, e.g., conjugated polymers or transparent polymers impregnated with dye molecules. Suitable exemplary colored polymers include polyaniline in the emeraldine and pernigraniline forms (deprotonated and half-deprotonated); P3HT (poly(3-hexyl)thiophene); and reduced PEDOT (poly(3,4-ethylenedioxythiophene)).

In some embodiments, the disclosed absorber elements may be distinguished from coating materials, e.g., a layer of a polymer, a layer of a biological material, a layer of silica, etc., which have been deposited on the surface of the microcavity. Thus, in some embodiments, the absorber element is not a coating material which has been deposited on the surface of the microcavity.

Figure 1:
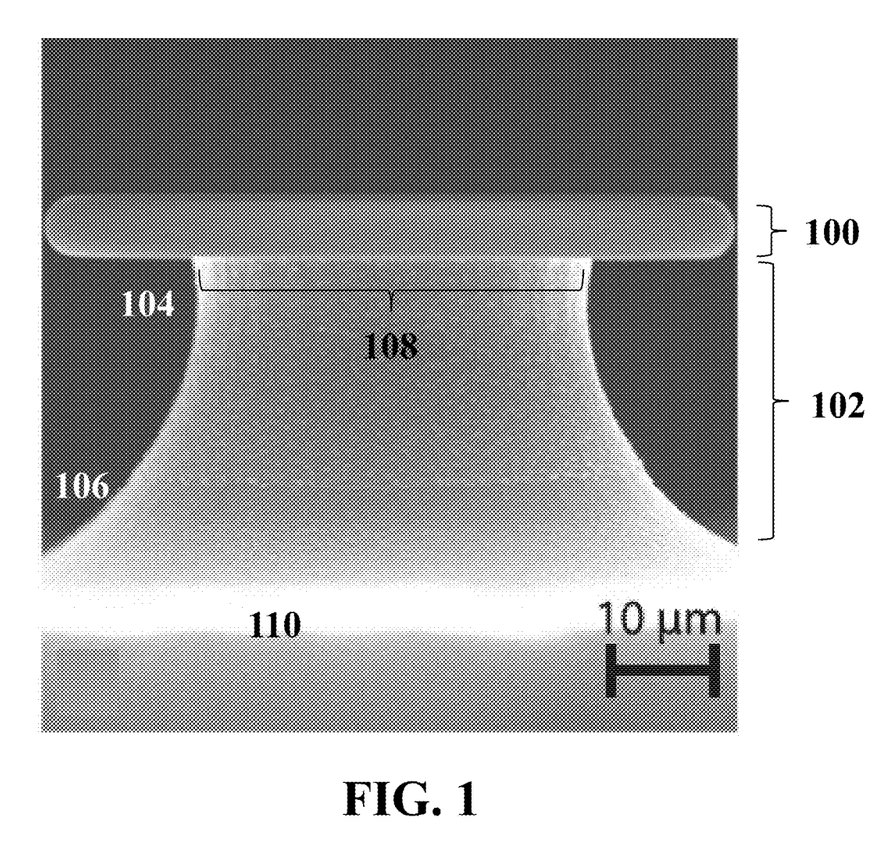
FIG. 1 shows a scanning electron microscope (SEM) image of a whispering gallery mode (WGM) optical microcavity configured as a toroid (standard toroid) in thermal contact with an absorber element configured as a pillar according to an illustrative embodiment.
Figure 2:
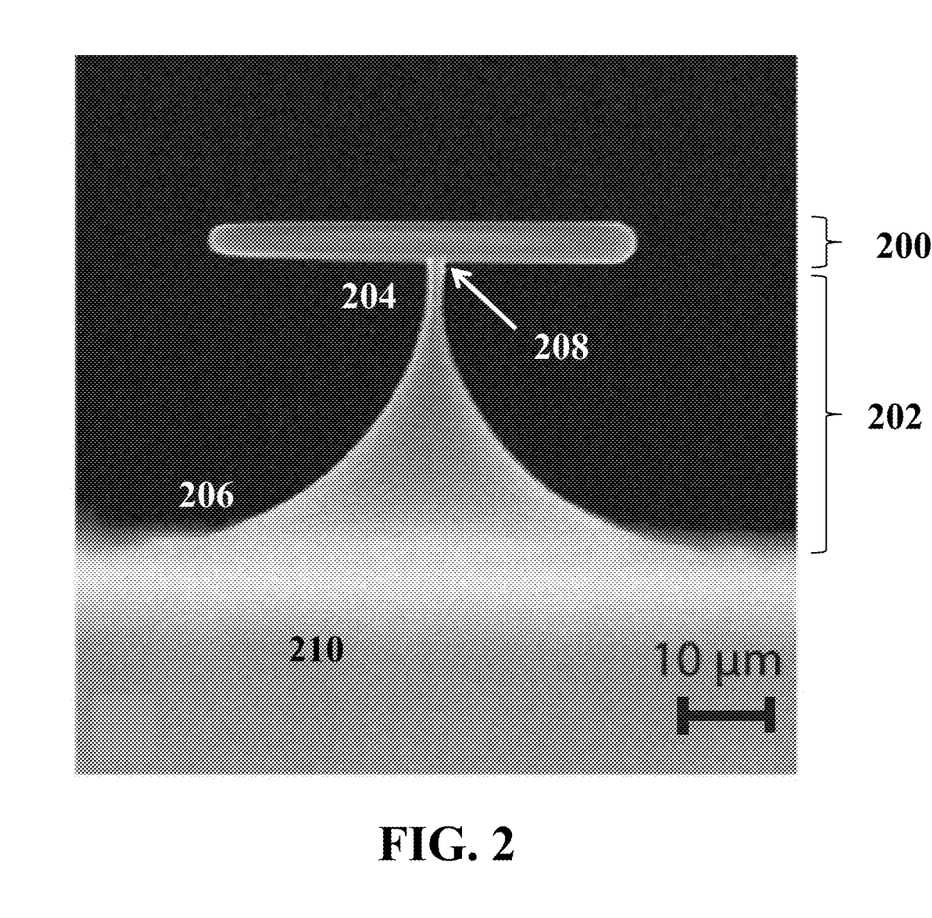
FIG. 2 shows a SEM image of a WGM optical microcavity configured as a toroid (re-etched toroid) in thermal contact with an absorber element configured as a pillar according to an illustrative embodiment.

FIGS. 1 and 2 show SEM images of WGM optical microcavities (100, 200) configured as a toroid in thermal contact with an absorber element (102, 202) configured as a pillar. The pillars have opposing ends (104, 106, 204, 206), with one end forming an interface (108, 208 with the microcavity (100, 200) and the other end merging with an underlying substrate (110, 210). The diameter of the pillar at the interface 108 is about 30 µm and the diameter of the pillar at the interface 208 is about 2 µm. In these embodiments, the dimensions of the pillar at the interface (108, 208) with the microcavity are different from the dimensions of the pillar at its opposing end (106, 206) as it merges into the underlying substrate (110, 210).

A probe laser beam is evanescently coupled into the optical microcavity. The selected wavelength of the probe laser beam generally depends upon the particular microcavity, which is characterized by resonance frequencies as described above. The selected wavelength of the probe laser beam can be that which substantially matches at least one resonance frequency of the microcavity, i.e., the wavelength can be substantially resonant with the microcavity. However, because the disclosed tuning methods allow for tuning of the microcavity's resonance frequencies, the selected wavelength of the probe laser beam need not match one of the microcavity's intrinsic resonance frequencies. The wavelength of the probe laser beam may be fixed or may be tuned (i.e., scanned) over a range of wavelengths. The probe laser beam may be evanescently coupled into the optical microcavity via a variety of techniques. A suitable technique is evanescent coupling via a tapered optical fiber.

A free space pump laser beam illuminates the absorber element. The free space pump laser beam can be delivered to the absorber element via a variety of techniques and optical components. However, by "free space" it is meant that the pump laser beam is not delivered to the absorber element via the propagating mode of the microcavity. A free space pump laser beam is one which is not evanescently coupled to the microcavity via the propagating mode. As further described below, a variety of optical components may be used to illuminate the absorber element with a free space pump laser beam, including microscope objectives, lens-tipped fiber optics or scanning microscopy tips. Thus, a free space pump laser beam can include beams which are delivered to the absorber element via a near-field interaction. The selected wavelength of the free space pump laser beam generally depends upon the particular absorber element. The selected wavelength of the free space pump laser beam can be that which achieves a desired amount of absorption of energy, e.g., maximal absorption, by the absorber element. Since the free space pump laser beam is not delivered to the absorber element via the propagating mode of the microcavity, the selected wavelength of the free space pump laser beam need not be a wavelength which matches a resonance frequency of the microcavity. Thus, the selected wavelength may be substantially non-resonant with the microcavity. However, wavelengths which are resonant with the microcavity may also be used. The wavelength of the free space pump laser beam may be fixed or may be tuned (i.e., scanned) over a range of wavelengths. Since the free space pump laser beam is not delivered to the absorber element via the propagating mode of the microcavity, a broad range of wavelengths may be used. Suitable wavelengths include wavelengths in the range of from about 300 nm to about 1100 nm.

The free space pump laser beam may be characterized by an intensity, which may be adjusted by adjusting the power of the laser beam and/or the focal spot size of the laser beam. Different intensities may be used, e.g., the intensity can be selected to achieve a desired shift in the resonance frequency of the microcavity. In some embodiments, the diameter of the focal spot of the free space pump laser substantially matches the width of an absorber element configured as a pillar. In some embodiments, the ratio of the diameter of the microcavity to the diameter of the focal spot size of the free space pump laser beam is at least about 10. This includes embodiments in which the ratio is at least about 20 or at least about 30. In some embodiments, the free space pump laser beam is focused to a diffraction-limited focal spot. The position of the free space pump laser beam may be defined as the position of its focal spot with respect to the propagating mode in the microcavity. In some embodiments, the focal spot does not substantially overlap with the propagating mode in the microcavity.

In another aspect, an apparatus is provided which comprises a whispering gallery mode optical microcavity, the microcavity characterized by at least one resonance frequency; optical components configured to evanescently couple a probe laser beam into the microcavity; an absorber element in thermal contact with the microcavity; and optical components configured to illuminate the absorber element with a free space pump laser beam, wherein the absorber element is configured to absorb energy from the free space pump laser beam, thereby generating heat, and to transfer the heat to the microcavity, thereby inducing a shift in the at least one resonance frequency.

A variety of optical components may be associated with the probe laser beam, including optical components configured to receive the probe laser beam, to direct it towards the microcavity and to evanescently couple it into the microcavity (e.g., tapered optical fiber). Similarly, a variety of optical components may be associated with a pump laser beam, including optical components configured to receive a pump laser beam, direct it towards the absorber element and to deliver it or focus it onto the absorber element. For example, microscope objectives, lens-tipped fiber optics or scanning microscopy tips may be used to focus a pump laser beam onto the absorber element. These exemplary optical components do not deliver the pump laser beam to the absorber element via the propagating mode of the microcavity and thus, provide for illumination of the absorber element with a "free space pump laser beam." Other optical components associated with the pump laser beam can include gimbal-mounted mirrors, relay optics, micro-mirror arrays and diffractive optics to control the position of the focal spot of the free space pump laser beam or beams with respect to the microcavity and the absorber element. The apparatus may comprise additional optical components typically used for manipulating laser beams, e.g., components for phase modulation, amplitude modulation and polarization control. The apparatus may comprise components configured to lock the probe laser beam to a resonance frequency of the microcavity via the Pound-Drever-Hall (PDH) technique. If a tapered optical fiber is used to evanescently couple the probe laser beam into the microcavity, the apparatus may comprise a piezo-positioning system to align the tapered optical fiber with the microcavity. The apparatus may comprise other components for evanescent coupling, including other waveguides incorporated into the device.

The apparatus may further comprise light sources (e.g., light emitting diodes (LEDs) or lasers) configured to generate the probe laser beam and the free space pump laser beam. In some embodiments of the disclosed methods and apparatuses, non-laser light sources may be used such that the term "laser beam" as used herein can be replaced with the term "light beam," i.e., a light beam from a non-laser light source. However, in other embodiments, the light source(s) are configured to generate true laser beams. The apparatus may further comprise a detector configured to detect light from the probe laser beam transmitted through the microcavity. The detector may be configured to provide as output, the power of the transmitted light. The apparatus may further comprise multiple evanescently coupled waveguides configured to allow photothermal switching between multiple probe wavelengths. For example, the apparatus may further comprise optical components configured to evanescently couple multiple probe laser beams having different wavelengths into the microcavity. Using the disclosed tuning methods, the free space pump laser beam can be used to tune the resonance frequency of the microcavity and to switch between these different wavelengths, i.e., to select which of the different wavelengths is resonant with the microcavity. The apparatus may comprise an array of whispering gallery mode optical microcavities, each microcavity in thermal contact with an absorber element. Each of the microcavities in the array may be independently tuned using the disclosed methods. As such, the apparatus may further comprise microlenses to focus multiple independently controlled free space pump laser beams onto multiple microcavities.

The apparatuses may be characterized by resonance tuning properties, including tuning ratio and switching speed. Tuning ratio provides a measure of the magnitude of the shift of resonance frequency that can be achieved at a particular power of the free space pump laser beam. In some embodiments, the tuning ratio is at least about 3000 fm/mW. This includes embodiments in which the tuning ratio is at least about 5000 fm/mW, at least about $1\times10^4$ fm/mW, at least about $1.5\times10^4$ fm/mW, at least about $1\times10^5$ fm/mW, at least about $1.5\times10^5$ fm/mW, or at least about $2\times10^5$ fm/mW. Switching speed provides a measure of how fast a particular shift of resonance frequency may be achieved. In some embodiments, the switching speed is at least about 350 Hz. This includes embodiments in which the switching speed is at least about 500 Hz, at least about 1 kHz, at least about 2 kHz, at least about 4 kHz, at least about 5 kHz, at least about 100 kHz, at least about 250 kHz, or at least about 500 kHz. These switching speeds can refer to the switching speed measured at a particular power of the free space pump laser beam (e.g., 1 μW or 1 mW). These switching speeds can also refer to the switching speed measured for a particular resonance shift (e.g., no more than 30 linewidths or no more than 7 linewidths). The apparatus may further comprise a cooling element in thermal contact with the microcavity configured to cool the microcavity after the temperature of the microcavity has increased due to heat transferred to it from the absorber element. A suitable exemplary cooling element is a body of liquid in contact with the surface of the microcavity. The cooling element may increase the cooling rate of the microcavity such that a higher switching speed can be obtained as compared to the apparatus without the cooling element for a given power of the free space pump laser beam.

The resonance tuning methods and apparatuses for carrying out the resonance tuning methods will find use in a variety of optoelectronic applications and devices, including optical switching. For an optical switching application, additional components may be included in the apparatuses as described in H. Rokhsari and K. J. Vahala, "Ultralow Loss, High Q, Four Port Resonant Couplers for Quantum Optics and Photonics," *Physical Review Letters*, Vol. 92, No. 25, Jun. 25, 2004.

The disclosed methods and apparatuses will be understood more readily by reference to the following examples, which are provided by way of illustration and are not intended to be limiting.

EXAMPLE

Resonance Tuning of Toroid Microcavities: This example demonstrates the tuning of the resonance of a toroid microcavity by modulating the position and intensity of a free-space visible, continuous wave (CW) pump laser whose output has been focused onto the resonator. By varying the power of the pump laser, a tuning ratio of $1.5\times10^5$ fm/mW was achieved on a silica toroid with a 2 μm diameter silicon pillar. A fraction of the heat generated from the silicon absorption is transferred to the silica, redshifting the resonant frequencies due to the positive thermo-optic coefficient of silica.

Toroidal microcavities are fabricated according to the procedure of D. K. Armani, T. J. Kippenberg, S. M. Spillane, and K. J. Vahala, Nature 421, 925 (2003) with a modification from J. B. Jager, V. Calvo, E. Delamadeleine, E. Hadji, P. Noe, T. Ricart, D. Bucci, and A. Morand, Appl. Phys. Lett. 99, 181123 (2011). Discs of thermally grown oxide 60 μm in diameter and 2 μm tall were patterned on silicon. A $SF_6$/Ar ICP etch was used to create a highly repeatable undercut in the silica disc. A $CO_2$ laser was used to selectively anneal the toroids (termed standard toroids). An additional etching step using $XeF_2$ vapor was optionally used to increase the undercut after the laser annealing step (termed re-etched toroids). (See M. Hossein-Zadeh and K. J. Vahala, Opt. Express 15, 166 (2007).) Q-factor $>10^7$ was measured on multiple re-etched toroids, indicating that the re-etching step did not compromise the ultrahigh Q-factor. A standard toroid 100 is shown in FIG. 1 and a re-etched toroid 200 is shown in FIG. 2.

An external cavity diode laser (New Focus, 1560 nm) was coupled into toroids via tapered optical fiber. (See D. K. Armani, T. J. Kippenberg, S. M. Spillane, and K. J. Vahala, Nature 421, 925 (2003).) Typical coupled powers ranged from 40-150 nW to avoid nonlinear thermal effects. A fixed-wavelength CW diode laser (Blue Sky Research, 640 nm) was focused to a 2 µm diameter spot with a 40×0.75 NA microscope objective. A gimbal-mounted mirror positioned at an optical plane conjugate to the back aperture of the objective was used to control the position of the laser spot in the toroid plane.

Figure 9:
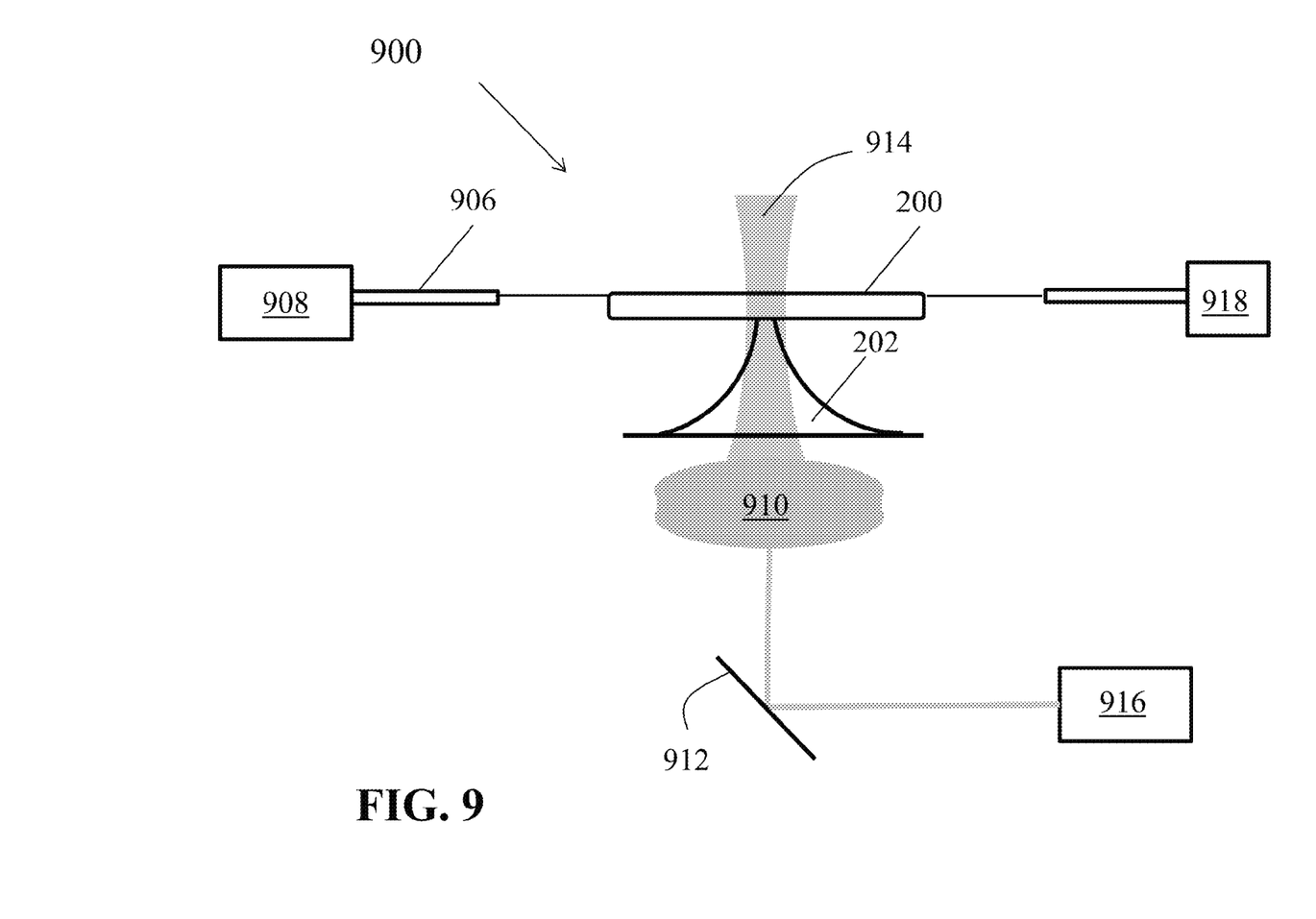
FIG. 9 depicts an apparatus for resonance tuning of a whispering gallery mode optical microcavity according to an illustrative embodiment.

The apparatus 900 used for resonance tuning in this example is schematically shown in FIG. 9. The apparatus 900 includes the whispering gallery mode optical microcavity 200 of FIG. 2 configured as a toroid in thermal contact with an absorber element 202 configured as a pillar. The apparatus 900 further includes optical components (e.g., the tapered optical fiber 906) configured to evanescently couple the probe laser beam generated by the external cavity diode laser 908 into the microcavity 200. The apparatus 900 further includes optical components (e.g., the microscope objective 910 and the gimbal-mounted mirror 912) configured to illuminate the absorber element 202 with the free space pump light beam 914 generated by the fixed-wavelength CW diode laser 916. The apparatus 900 further includes a detector 918 configured to detect light from the probe laser beam transmitted through the microcavity 200.

Figure 3A:
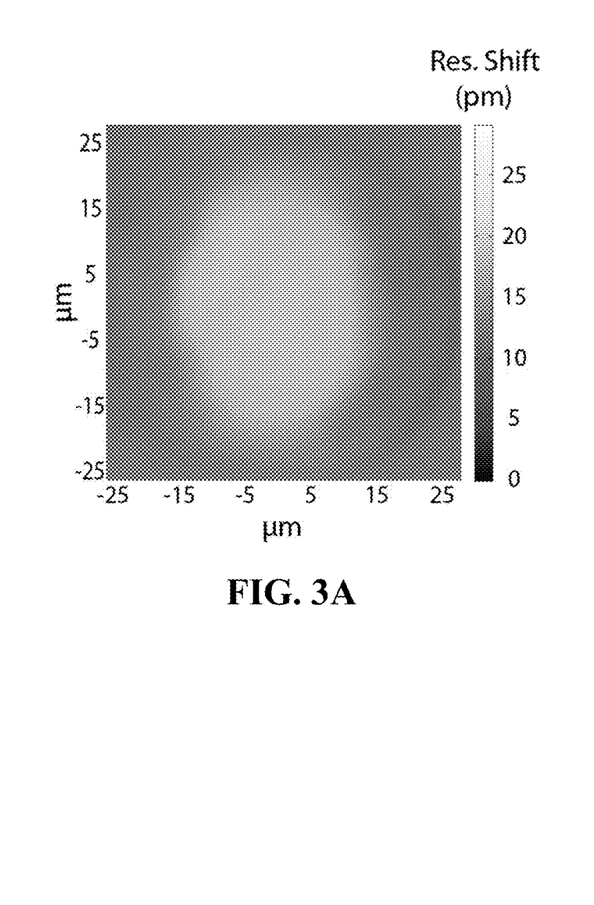
Figure 3B:
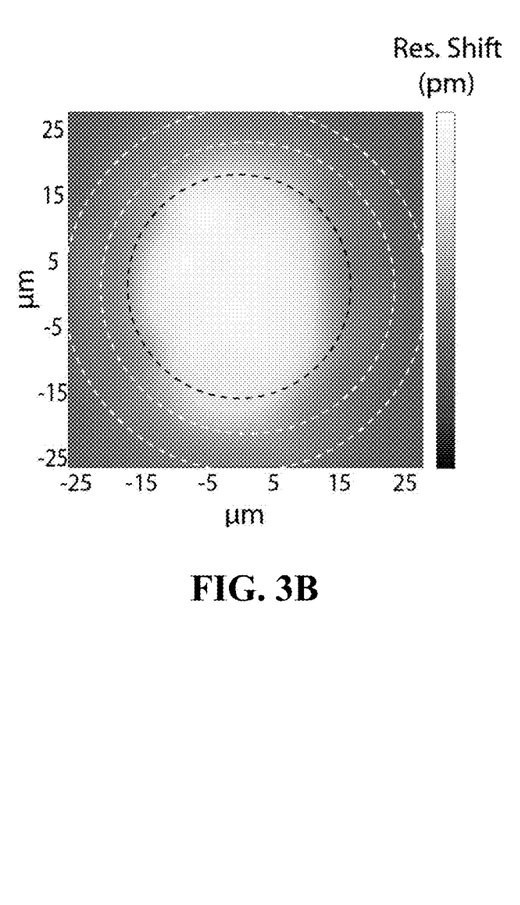
Figure 4A:
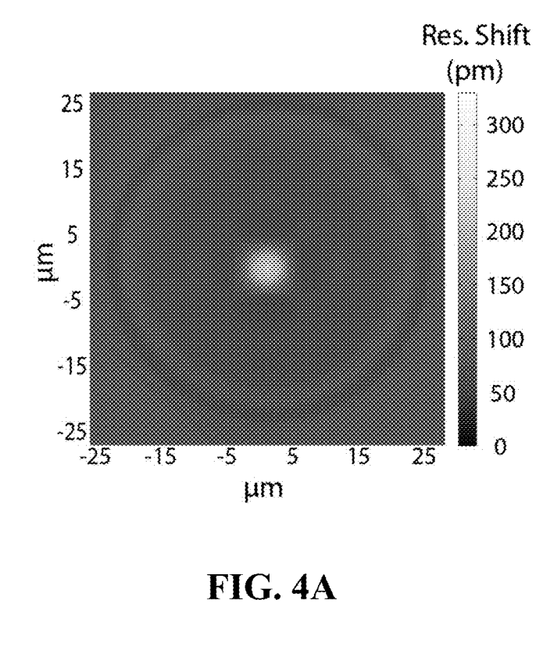
Figure 4B:
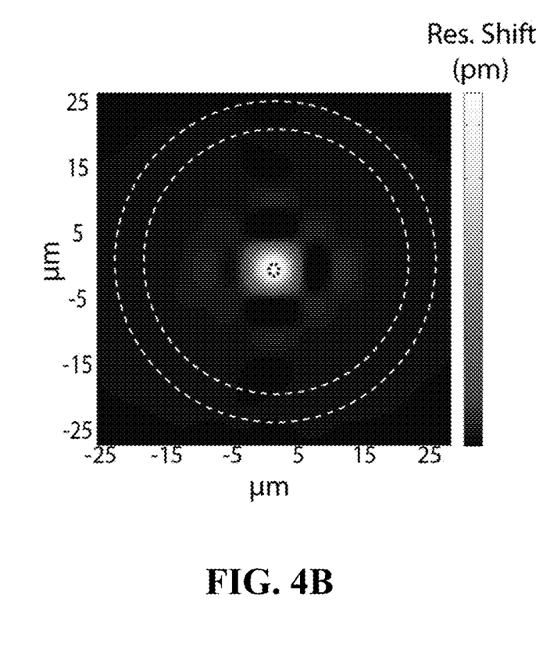
Figure 5:
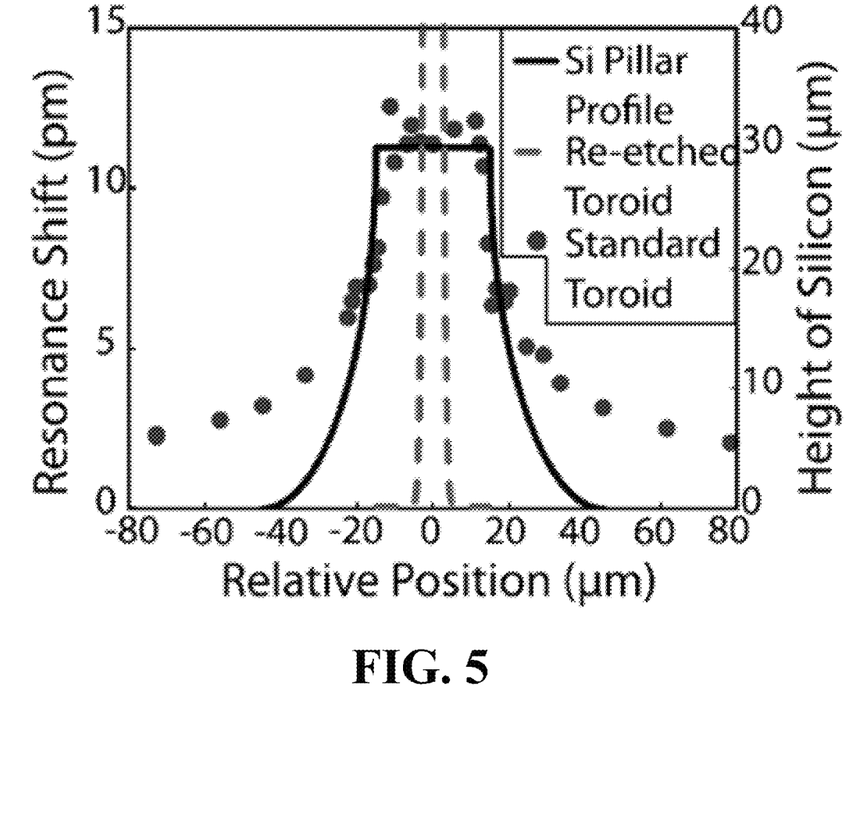
FIG. 5 shows photothermal linescans of a standard and re-etched toroid. The laser spot was scanned laterally across the center of the toroid at constant power (4.2 mW absorbed) and the resonance shift measured as a function of laser position. The profile of the silicon pillar is shown for the standard toroid (black), the resonance shift is shown for the standard toroid (circles), and the resonance shift is shown for the re-etched toroid (dashed line). The re-etched toroid is significantly more sensitive.
Figure 6:
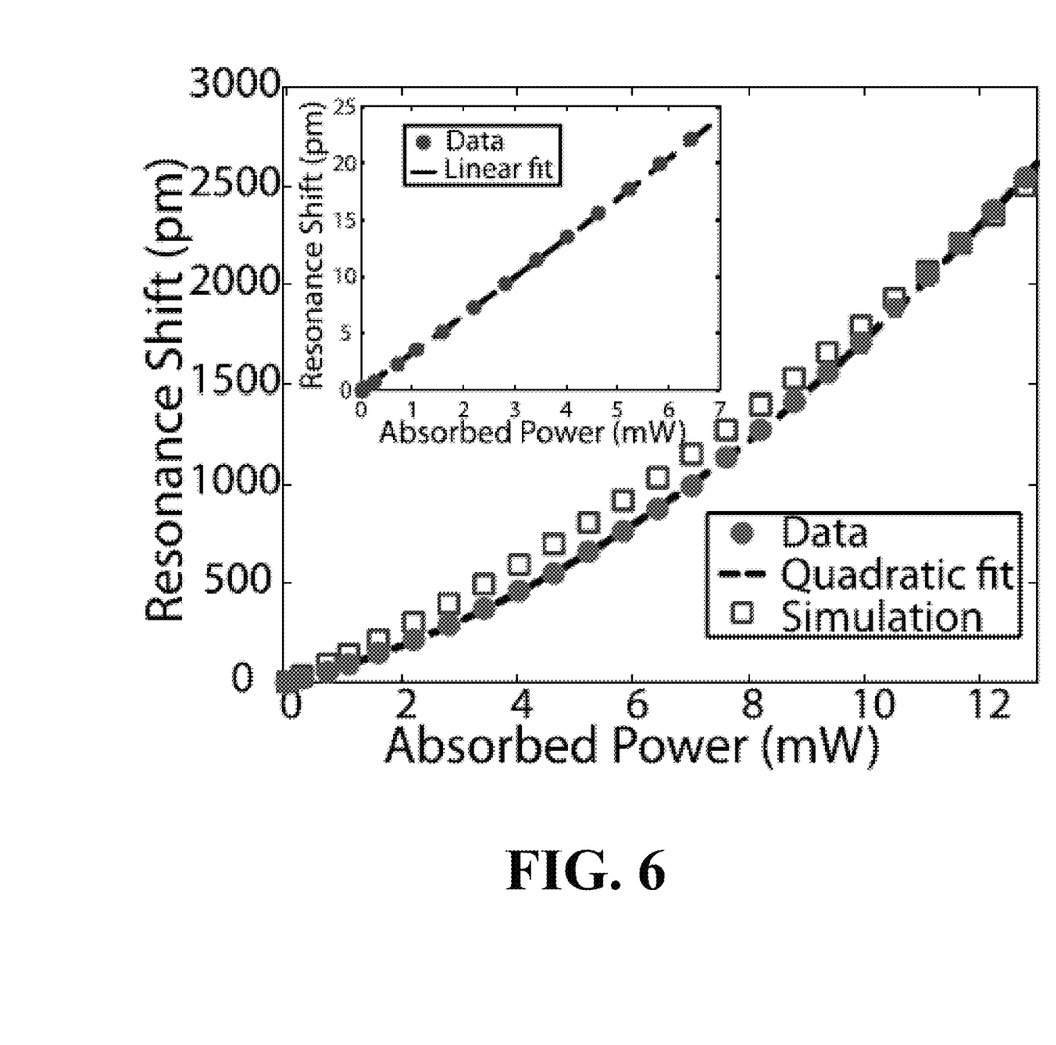
FIG. 6 shows the power dependence of photothermal shift. The shift is seen to be quadratic for a re-etched toroid and to extend to over half the free spectral range (FSR) of the resonator. Simulations capture the quadratic power dependence and were performed by calculating equilibrium temperature at the silica rim from the measured pump power and extrapolating resonance shift with Equation 1 (see Example, below). Error bars are present but too small to see on this scale. The inset shows the results for a standard toroid, showing a shallower slope and linearity over the range examined.

Resonance shift of the toroid was spatially mapped by scanning the pump beam over the resonator and surrounding area as shown in FIGS. 3 and 4. FIG. 3 is a photothermal map of the structure shown in FIG. 1 and FIG. 4 is a photothermal map of the structure shown in FIG. 2. The laser spot was small compared to the size of the resonator, enabling a high-resolution map. The maximum shift was closely associated with illuminating the silicon pillar where the shift was essentially constant with position. Resonance shift as a function of the position of the pump beam relative to the center of the toroids is shown in FIG. 5 for the re-etched toroid (dashed line) and the standard toroid (circles). Resonance shift as a function of power of the pump beam is shown in FIG. 6 for the re-etched toroid and the standard toroid (inset). The resonance shift, 3200 fm/mW pump power, was approximately five times larger on the silicon pillar than when the spot position was well-separated (80 µm) from the toroid. Decreasing the size (diameter) of the toroid support pillar with an additional etching step (re-etched toroid) significantly amplifies the effect and the slope rises to $1.5 \times 10^5$ fm/mW, without compromising the Q-factor. The high power density ($10^8$-$10^9$ W/cm$^3$) in the heated volume drives the high sensitivity of this tuning method. The increased sensitivity of the re-etched toroid is attributed to the reduced heat capacity of the smaller silicon pillar, leading to a greater temperature increase at the silicon-silica interface, and consequently greater equilibrium temperature at the mode-carrying silica.

To understand the relevant heat flows, numerical simulations were performed in COMSOL Multiphysics (the simulations are described in more detail below). The redshift in resonance wavelength ($\Delta\lambda$) as a function of the change in temperature is given by $$\lambda_T - \lambda_0 = \Delta\lambda = \frac{\lambda_0}{n_0} \times \frac{dn}{dT}(T) \times (T - T_0) \quad \text{Equation 1}$$

where $$\lambda_0 = 1.566 \, \mu m,$$
$$n_0 = 1.444$$

and $$\frac{dn}{dT}(T) = 2.6 \times 10^{-8} K^{-2} \times T + 7.5 \times 10^{-7} K^{-1},$$

an expression derived from linear extrapolation of data from V. S. Il'chenko and M. L. Gorodetskii, Laser Phys 2, 1004 (1992). As shown in FIG. 6 (squares), the model accurately matches the experimental power dependence. As shown in the inset of FIG. 6, over a tuning range of 0-25 µm for a standard toroid, the tuning curve is linear, with a slope of 9.2 µm/K. At the much greater shifts possible with a re-etched toroid, the shift appears quadratic in both simulations and experiments due to the temperature dependence of the thermo-optic Coefficient $$\left(\frac{dn}{dT}\right).$$

At 12.7 mW of pump laser power, the silica heats up to 443 K. At larger pump powers (>2 mW absorbed), the re-etched toroid resonances exhibited minor spectral fluctuations consistent with intensity noise in the pump laser.

Figure 7:
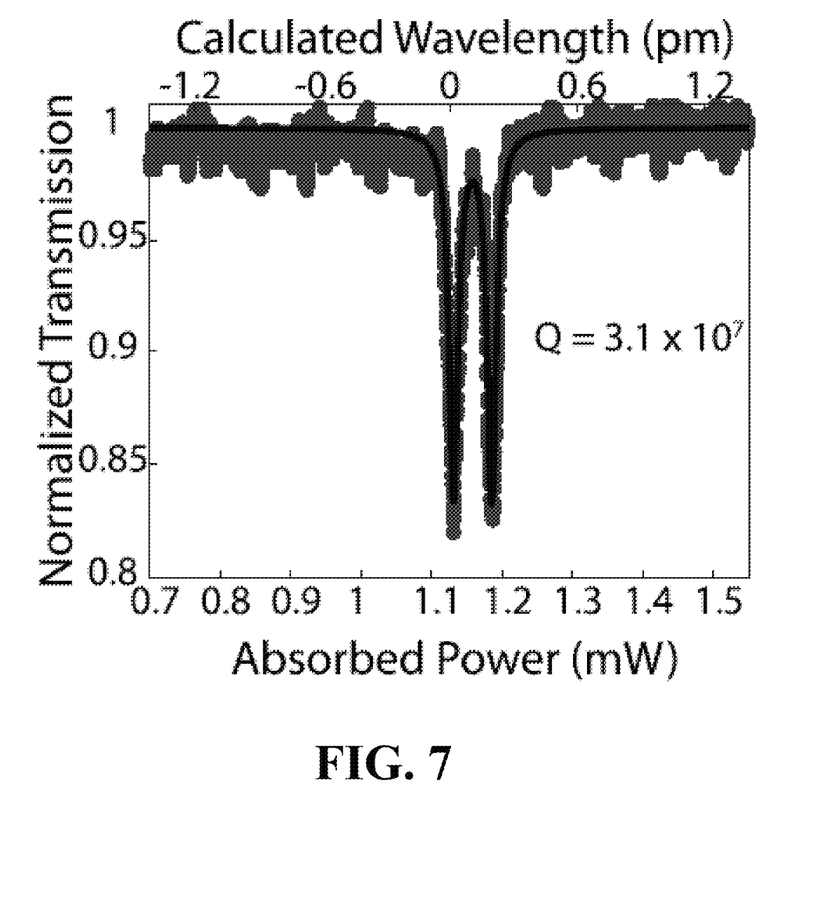
FIG. 7 shows a scan of toroid resonance shift versus photothermal heating, with Lorentzian fit. The probe wavelength was fixed at 1566.93 nm, while the pump laser power was scanned with a triangular waveform. The wavelength was calculated from the measured temperature dependence of the toroid resonance (3200 fm/mW).

The strengths of this approach are versatility of control and sensitivity. As shown in FIG. 6, continuous and convenient tuning of resonance position over more than one half of the resonator's free spectral range (FSR) has been demonstrated, limited by the power of the pump laser. Alternatively, as little as 1 µW shifts the resonance by one full width at half maximum (FWHM), a low-power switch. As a demonstration of the elimination of the need for a tunable probe, FIG. 7 shows that ultrahigh-Q factors are observed by photothermally tuning the resonance and probing at a fixed wavelength. The splitting of the resonance is caused by backscatter-induced degeneracy lifting of the clockwise and counterclockwise whispering gallery mode (WGM) and is routinely observed in toroidal microcavities. Control over multiple orders of magnitude of spectral position is a highly useful experimental parameter.

Figure 8:
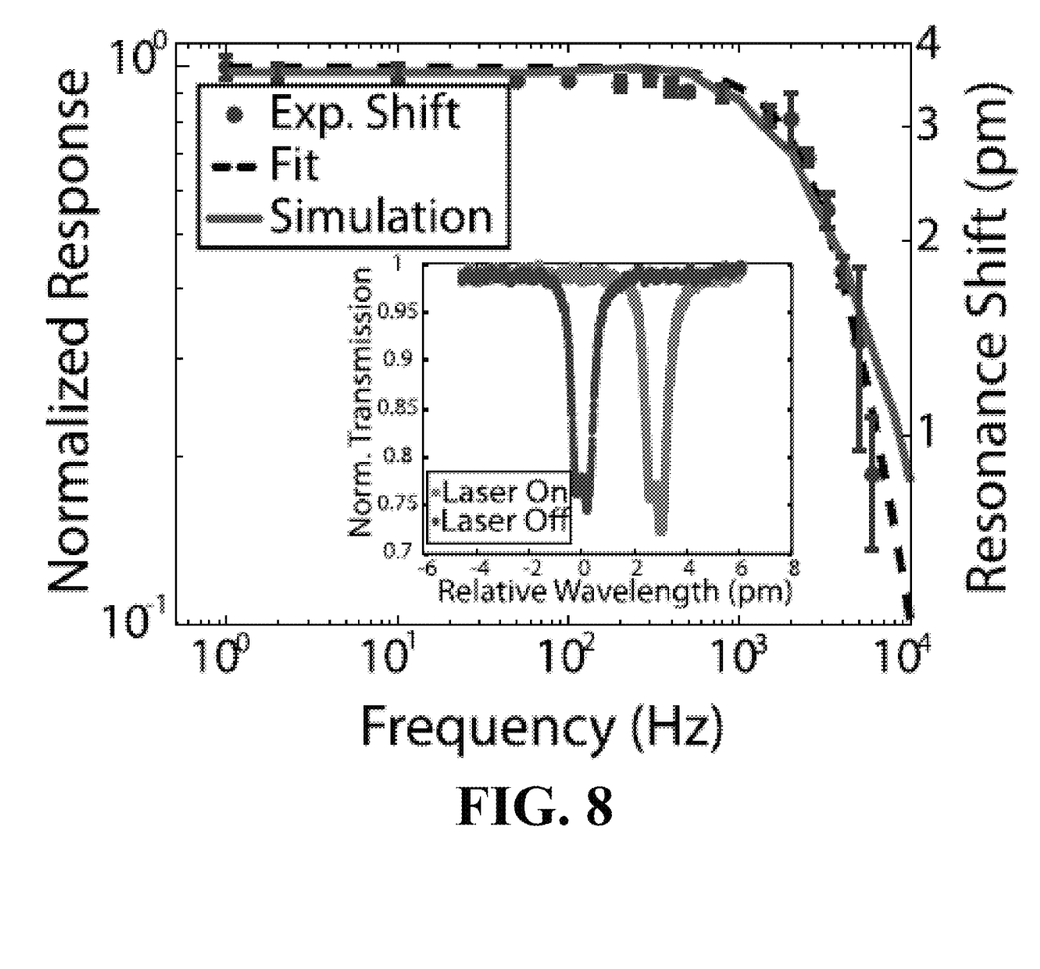
FIG. 8 shows the frequency response of a standard toroid during pump beam modulation (circles). The toroid has a cutoff frequency of 4200 Hz, and was fit with exponential time dependence (dashed line, $1-e^{(-t/\tau)}$). Simulation (solid line) predicts a cutoff frequency of 5000 Hz. The inset shows a scan of resonance with pump laser off (black) and on (grey).

The timescale of the resonance shift, a critical parameter for optical switching applications, was measured by modulating the pump beam with a square wave while recording the relative position of the modulated and un-modulated resonance. The maximum wavelength shift was set (by controlling the pump intensity) to 2.8 µm, ~30 linewidths for $Q=1.5 \times 10^7$. A shift of only several linewidths is sufficient for switching. When the time interval falls below the thermal equilibration time of the toroid the shift decreases. FIG. 8 shows a modified Bode magnitude plot of a standard toroid demonstrating a cutoff frequency of 4200 Hz, over an order of magnitude faster than previously reported thermal control mechanisms. (See D. Armani, B. Min, A. Martin, and K. J. Vahala, Appl. Phys. Lett. 85, 5439 (2004).) Time-dependent simulations predict a comparable cutoff of 5000 Hz on a standard toroid. The re-etched toroid has a lower cutoff frequency of 400 Hz, likely due to the larger path length for heat to travel through the silica between the silicon pillar and the silica rim.

In summary, a highly versatile method of tuning the resonance position of toroidal microcavities was demonstrated. A visible, fixed-wavelength laser at modest power was used to reproducibly shift the resonance by a few to more than 10,000 times the FWHM. This technique places few requirements on the wavelength, linewidth, or tunability of the pump beam. Re-etching the silicon pillar greatly increases the sensitivity without compromising the ultrahigh-Q. The re-etched toroid can be continuously tuned over half the FSR, with fast modulation times. These toroids can also be switched over one FWHM with approximately 1 µW of pump beam power, an important consideration for optical processing. This method reduces the need for expensive tunable probe sources, as now a simple and inexpensive pump laser can be used to shift the resonance of a microcavity to be resonant with a fixed wavelength probe.

Simulations: Photothermal effects on the toroid were modeled with the Heat Transfer Module of COMSOL Multiphysics. The physical dimensions of the toroid were extracted from side-view SEM images (see FIGS. 1 and 2). Air around the toroid and a silicon substrate were included. Heating by the pump laser was modeled by a series of five 1-µm thick cylindrical heat sources of decreasing intensity. The total heat generated was equal to the incident optical power adjusted by the measured reflectivity of 2 µm of thermal oxide on silicon at 640 nm (R=0.24). The heat was divided among the five heating regions with a decaying exponential corresponding to the penetration depth of 640 nm light in silicon. The volume of silicon heated by the laser was approximately 10 µm$^3$, given by the product of the spot size and penetration depth in silicon at 640 nm (3.3 µm). Equilibrium temperature was calculated by solving for the stationary solution to conductive heat transfer. Convection was found to negligibly affect the observed temperature increase (<1%), and was not included in the simulations. Material properties, except for the thermo-optic coefficient (discussed below) were taken from the COMSOL library. Small changes in the size distribution of the heat sources were found to contribute only minor variations to calculated thermal properties. Resonance shifts were calculated from the equilibrium temperature of the silica rim, which was found to be highly uniform with the pump beam centered on the toroid. The thermal expansion of silica is an order of magnitude smaller than the thermo-optic effect and was neglected in these calculations. (See J. W. Berthold, S. F. Jacobs, and M. A. Norton, Metrologia 13, 9 (1977).) In the low-power regime the thermo-optic coefficient of the silica can be assumed to be constant, with a value of $8.5*10^{-6}$/K. (See Douglas B. Leviton and Bradley J. Frey, Proc. SPIE-Int. Soc. Opt. Eng. 6273, 62732K (2006).) At greater shifts the temperature dependence of the thermo-optic coefficient had to be accounted for (see FIG. 6 and above). Time-dependent simulations were conducted with all the parameters identical to the stationary simulations.

Reproducibility and Stability: Subtle differences in fabrication conditions, including the $CO_2$-reflow process, resulted in differences between the tuning curves of individual toroids. Data showed the variation in spatial linescans between four unique standard toroids. The peak resonance shift at constant power (4.1 mW absorbed) yielded the slope-to-slope variation in photothermal tuning between toroids. The slope varied by as much as 35% between toroids. However, the shape of the linescan did not vary between different toroids. Importantly, slope-to-slope variations of the tuning curve do not constitute a disadvantage of the approach presented in this example, as individual toroids can still be conveniently controlled.

Measuring the Q-factor of toroidal resonances by photothermally tuning the resonance wavelength and probing at a fixed wavelength was comparable to the traditional method of scanning the wavelength of the probe laser with no pump beam. As described above, FIG. 7 was obtained via photothermal tuning. The same resonance on the same toroid was measured on a different day, via wavelength scanning. The measured Q-factor ($1.5 \times 10^7$) was not significantly different.

Using the pump beam to offset the resonance wavelength did not significantly change the Q-factor. A transmission spectrum of a re-etched toroid was obtained under pump beam illumination (4.1 mW absorbed, the same power used in the photothermal maps of FIGS. 3 and 4). Although the center wavelength of the resonance shifted by 460 µm relative to the unperturbed resonance, the Q-factor remained essentially the same ($2.2 \times 10^7$) as compared to the measurement at zero photothermal shift ($1.5 \times 10^7$) or the measurement by photothermally tuning the resonance at low power ($3.1 \times 10^7$, FIG. 7). In this case, a singlet was seen, consistent with the stochasticity of resonance splitting.

Stability of the resonance wavelength under weak or moderately intense pump beam illumination did not greatly differ from that with no pump beam. Scan-to-scan shifts in the center wavelength of the resonance measured at zero photothermal shift yielded a standard deviation in peak center position of 33 fm with no pump power (resonance FWHM was 51 fm) and increased to 70 fm at 1.2 mW absorbed pump power, a modest increase given the large offset (~2,500 linewidths).

As mentioned above, fluctuations in the resonance position were observed when pumping re-etched toroids with higher pump beam power. A representative transmission scan of the toroid resonance at 4.1 mW absorbed power was obtained in which the wavelength of the probe laser was scanned over a 5.3 µm range in 50 ms. The resonance position changed, and crossed the scanning wavelength of the probe laser several times during the scan, although ultrahigh Q-factor was maintained ($Q > 1 \times 10^8$). This scan suggests that the resonance shifts on a timescale faster than the scan speed (5.3 µm in 50 ms), but remains essentially constant in the time it takes to cross over a single resonance (~190 us to cover ~20 fm). Such fluctuations were not observed on standard toroids, and were not observed at low power on the re-etched toroid. Characterization of the pump laser intensity revealed the presence of moderate (up to several %) and intermittent intensity fluctuations that varied over multiple time scales from us to ms. At the 4.1 mW pump in the transmission scan, variations in pump power of 1% would result in peak shifts of several pm, consistent with what was observed. These fluctuations were also found to vary with the tension on the fiber optic taper, increasing when the taper loosened and decreasing when it was tightened. When tensioned, the shifts were partially but not completely mitigated. It is likely that the fast and intermittent variations in pump intensity of the pump diode laser were the dominant contributor to these fluctuations.

Frequency Response: The frequency response of re-etched toroids to pump beam modulation was investigated. A much lower cutoff frequency was observed (400 Hz vs. 4200 Hz in a standard toroid). This is attributed to the much smaller interfacial region between the silicon pillar and the bulk silicon of the underlying substrate, which constricts the rate of heat transfer between the toroid and the underlying substrate. This is consistent with the much higher temperatures achieved at the same pump power on re-etched toroids.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more". Still further, the use of "and" or "or" is intended to include "and/or" unless specifically indicated otherwise.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art, all language such as "up to," "at least," "greater than," "less than," and the like includes the number recited and refers to ranges which can be subsequently broken down into subranges as discussed above. Finally, as will be understood by one skilled in the art, a range includes each individual member.

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. An apparatus comprising:
    (a) a whispering gallery mode optical microcavity, the microcavity characterized by at least one resonance frequency;
    (b) optical components configured to evanescently couple a probe laser beam into the microcavity;
    (c) an absorber element in thermal contact with the microcavity;
    (d) and optical components configured to illuminate the absorber element with a free space pump light beam, wherein the absorber element is configured to absorb energy from the free space pump light beam, thereby generating heat, and to transfer the heat to the microcavity, thereby inducing a shift in the at least one resonance frequency,
    and further wherein the absorber element is configured as a pillar forming an interfacial region with the microcavity at one of the ends of the pillar.

2. The apparatus of claim 1, wherein the pillar is composed of a material which is different from the material of the microcavity.

3. The apparatus of claim 2, wherein the pillar is composed of silicon.

4. The apparatus of claim 1, wherein the width of the pillar is no more than about 20 μm.

5. The apparatus of claim 1, wherein the width of the pillar is in the range of from about 25 μm to about 35 μm.

6. The apparatus of claim 1, wherein the surface of the microcavity is substantially free of a coating material.

7. The apparatus of claim 1, wherein the microcavity is a toroid.

8. The apparatus of claim 7, wherein the surface of the microcavity is substantially free of a coating material.

9. The apparatus of claim 7, wherein the width of the pillar is no more than about 20 μm.

10. The apparatus of claim 9, wherein the surface of the microcavity is substantially free of a coating material.

11. The apparatus of claim 1, wherein the apparatus is characterized by a tuning ratio of at least about $1 \times 10^5$ fm/mW.

12. The apparatus of claim 1, wherein the apparatus is characterized by a switching speed of at least about 4 kHz as measured for a shift of no more than about 30 linewidths at about 1 mW of power of the free space pump light beam.

13. An apparatus comprising:
    (a) a whispering gallery mode optical microcavity, the microcavity characterized by at least one resonance frequency;
    (b) optical components configured to evanescently couple a probe laser beam into the microcavity;
    (c) an absorber element in thermal contact with the microcavity;
    (d) and optical components configured to illuminate the absorber element with a free space pump light beam, wherein the absorber element is configured to absorb energy from the free space pump light beam, thereby generating heat, and to transfer the heat to the microcavity, thereby inducing a shift in the at least one resonance frequency,
    and further wherein the surface of the microcavity is substantially free of a coating material.

14. The apparatus of claim 13, wherein the absorber element is configured as a pillar forming an interfacial region with the microcavity at one of the ends of the pillar and the width of the pillar is no more than about 20 μm.

15. The apparatus of claim 13, wherein the width of the pillar is in the range of from about 25 μm to about 35 μm.

16. A method comprising:
    (a) evanescently coupling a probe laser beam into a whispering gallery mode optical microcavity, the microcavity characterized by at least one resonance frequency; and
    (b) illuminating an absorber element in thermal contact with the microcavity with a free space pump light beam, the absorber element configured to absorb energy from the free space pump light beam, thereby generating heat, and to transfer the heat to the microcavity, thereby inducing a shift in the at least one resonance frequency,
    wherein the absorber element is configured as a pillar forming an interfacial region with the microcavity at one of the ends of the pillar.

17. The method of claim 16, wherein the wavelength of the free space pump light is substantially non-resonant with the resonance frequencies of the microcavity.

18. The method of claim 16, wherein a focal spot of the free space pump light beam does not substantially overlap with the propagating mode in the microcavity.

19. The method of claim 16, wherein the diameter of a focal spot of the free space pump light substantially matches the width of the pillar.

20. The method of claim 16, wherein the ratio of the diameter of the microcavity to the diameter of a focal spot of the free space pump light beam is at least about 10.

* * * * *